US008569255B2

(12) United States Patent
Wong

(10) Patent No.: US 8,569,255 B2
(45) Date of Patent: Oct. 29, 2013

(54) POST-EXPOSURE THERAPY OF INFLUENZA A INFECTIONS

(75) Inventor: Jonathan P. Wong, Medicine Hat (CA)

(73) Assignee: Her Majesty the Queen in Right of Canada, as represented by the Minister of National Defence, Ontario (CA)

( * ) Notice: Subject to any disclaimer, the term of this patent is extended or adjusted under 35 U.S.C. 154(b) by 0 days.

(21) Appl. No.: 13/364,486

(22) Filed: Feb. 2, 2012

(65) Prior Publication Data

US 2012/0195960 A1 Aug. 2, 2012

Related U.S. Application Data

(60) Provisional application No. 61/438,704, filed on Feb. 2, 2011.

(51) Int. Cl.

| | |
|---|---|
| *C12N 15/11* | (2006.01) |
| *A61K 48/00* | (2006.01) |
| *C07H 21/04* | (2006.01) |

(52) U.S. Cl.
USPC ....... 514/44 A; 514/44 R; 536/23.4; 536/24.5

(58) Field of Classification Search
None
See application file for complete search history.

(56) References Cited

U.S. PATENT DOCUMENTS

| | | | |
|---|---|---|---|
| 6,468,558 | B2 | 10/2002 | Wong |
| 6,544,958 | B2 | 4/2003 | Wong et al. |
| 2001/0007667 | A1 | 7/2001 | Wong |
| 2006/0223742 | A1 | 10/2006 | Salazar |
| 2007/0160632 | A1 | 7/2007 | Haixiang |
| 2008/0131398 | A1 | 6/2008 | Jeffs et al. |
| 2008/0161324 | A1 | 7/2008 | Johansen et al. |
| 2008/0317811 | A1 | 12/2008 | Andre et al. |
| 2009/0087454 | A1 | 4/2009 | Salazar |
| 2009/0214638 | A1 | 8/2009 | Wong |
| 2009/0247481 | A1 | 10/2009 | Nguyen et al. |
| 2010/0009970 | A1 | 1/2010 | Johansen et al. |
| 2010/0081713 | A1 | 4/2010 | Sharma et al. |
| 2010/0092479 | A1 | 4/2010 | Johansen et al. |
| 2010/0266680 | A1 | 10/2010 | Andre et al. |

FOREIGN PATENT DOCUMENTS

| | | |
|---|---|---|
| WO | 03-016572 | 2/2003 |
| WO | 2005-102278 | 11/2005 |

OTHER PUBLICATIONS

Bright RA, Medina MJ, Xu X, et al. (2005) Incidence of adamantine resistance among influenza A (H3N2) viruses isolated worldwide from 1994 to 2005: a cause for concern. Lancet. 366(9492), 1175-1181.
Christopher ME, Wong JP (2008) Broad-Spectrum Drugs Against Viral Agents. Int. J. Mol. Sci. 9, 1561-1594.
de Jong MD, Tran TT, Truong HK, et al. (2005) Oseltamivir resistance during treatment of influenza A (H5N1) infection. N. Engl. J. Med. 353(25), 2667-2672.
Dharan NJ, Gubareva LV, Meyer JJ, et al. (2009) Infections with oseltamivir-resistant influenza A (H1N1) virus in the United States. JAMA. 301(10), 1034-1041.
Dow S. (2008) Liposome-nucleic acid immunotherapeutics. Expert Opinion on Drug Delivery. 5(1), 11-24.
Kumar A, Zarychanski R, Pinto R, et al. (2009) Critically ill patients with 2009 influenza A (H1N1) infection in Canada. JAMA. 302(17), 1872-1879.
Mizuta T, Fujiwara M, Hatta T, Abe T, Miyano-Kurosak N, Shigeta S, Yokota T, Takaku H. (1999) Antisense oligonucleotides directed against the viral RNA polymerase gene enhance survival of mice infected with influenza A. Nature Biotechnology. 17, 583-587.
Saravolac EG, Wong JP. (2007) Recent Patents on Development of Nucleic Acid-based Antiviral Drugs against Seasonal and Pandemic Influenza Virus Infections. Recent Patents on Anti-Infective Drug Discovery. 2, 140-147.
Wong JP, Saravolac EG, Sabuda D, Levy HB, Kende, M. (1995) Prophylactic and therapeutic efficacies of poly(ICLC) against respiratory influenza A virus infection in mice. Antimicrob. Agents Chemother. 39, 2574-2576.
Wong JP, Christopher ME, Salazar AM, Dale RMK, Sund L-Q, Wang M. (2007) Nucleic acid-based antiviral drugs against seasonal and avian influenza viruses. Vaccine. 25, 3175-3178.
Wong JP, Christopher ME, Viswanathana S, Karpoff N, Daia X, Dasa D, Sun LQ, Wang M, Salazar AM. (2009a) Activation of toll-like receptor signaling pathway for protection against influenza virus infection. Vaccine. 27, 3481-3483.
Wong JP, Christopher ME, Viswanathan S, Dai X, Salazar AM, Sun L-Q, Wang M. (2009b) Antiviral Role of Toll-Like Receptor-3 Agonists Against Seasonal and Avian Influenza Viruses. Current Pharmaceutical Design. 15(11), 1269-1274.

Zhang T, Zhao P, Zhang W, Liang M, Gao Y, Yang S, Wang T, Qina C, Wang C, Xia X. (2010) Antisense oligonucleotide inhibits avian influenza virus H5N1 replication by single chain antibody delivery system. Vaccine. doi:10.1016, 7 pages.

*Primary Examiner* — Dana Shin

(74) *Attorney, Agent, or Firm* — Shelly Guest Cermak; Cermak Nakajima LLP

(57) ABSTRACT

Poly ICLC or liposome-encapsulated Poly ICLC (LE Poly ICLC) in combination with antisense oligonucleotides (AS) act synergistically in post-exposure prophylaxis or therapy of influenza infections, especially H5N1 virus infections.

13 Claims, 3 Drawing Sheets

POST-EXPOSURE THERAPY OF INFLUENZA A INFECTIONS

CROSS-REFERENCE TO RELATED APPLICATIONS

This application claims the benefit of U.S. Ser. No. 61/438,704 filed Feb. 2, 2011, the entire contents of which is herein incorporated by reference. Also, the Sequence Listing filed electronically herewith is hereby incorporated by reference (File name: 2012-02-02T_1036-0001_Seq List; File size: 2 KB; Date recorded: Feb. 2, 2012).

FIELD OF THE INVENTION

The present invention relates to compositions and methods for post-exposure treatment of viral infections, particularly influenza A virus infections.

BACKGROUND OF THE INVENTION

Influenza viruses are etiological agents of deadly flu that continue to pose global health threats and have caused global pandemics that killed millions of people worldwide. The global crisis posed by the emergence of the avian H5N1 influenza virus provides testament to the challenges of defending against a deadly virus that is unpredictable and ever changing. As the human death toll from the bird flu outbreaks continues to increase, the world is moving closer to a potential influenza pandemic. With a reported case fatality over 50%, an influenza pandemic by a highly transmissible strain of avian H5N1 influenza virus could potentially kill millions of people worldwide.

There are a number of commercially available antiviral drugs which can be considered as the first line of defense against seasonal or avian influenza infections. There are two conventional influenza drugs, namely amantadine and rimantadine, which have been used clinically to reduce the severity and duration of seasonal flu. These compounds arc M2 ion-channel blocking adamantine derivatives that work by interfering with viral uncoating inside the cells. In recent years, good advances have been made in the development of anti-influenza drugs, particularly the development of neuramidase inhibitors, namely Tamiflu™ (Zanamivir) [4-acetamido-5-amino-3-(1-ethylpropoxyl)-1-cyclohexene-1-carboxylic acid ethyl ester (invented by Gilead Sciences and marketed by Roche AG, and Relenza™ (Oseltamivir) (4-guanidino-Neu5Ac2en) (marketed by Glaxo-SmithKline). Neuraminidase is one of the glycoproteins present on the virus surface, and it is an enzyme that cleaves sialic acid residues from the receptors for the virus. The inhibition of this enzyme by Tamiflu™ and Relenza™ stops the spread of this virus and effectively suppresses infection.

One of the greatest challenges with current stockpiling of antiviral drugs as part of pandemic planning or bioterrorism defense is high level of drug-resistance of influenza viruses. Most seasonal human influenza strains (H3N2) are resistant to amantadine and rimantadine, thereby limiting their usefulness against seasonal influenza. When the distribution of genetic mutations associated with resistance of avian H5N1 influenza virus to amantadine and rimantadine was determined, it was found that more than 95% of isolates of avian H5N1 influenza from Thailand and Vietnam contained resistance mutations to these drugs. While many western nations are stockpiling drugs such as Tamiflu™ as part of the pandemic preparedness plan, there is a growing concern that the circulating avian flu virus may be resistant to Tamiflu™. Significant number of the avian flu clinical isolates from hard-hit areas in Vietnam had developed resistance to Tamiflu™. As global fears of a pandemic grow, the use of neuraminidase inhibitors against seasonal influenza has been shown to significantly increase, and this will lead to corresponding incidence of drug-resistance to these drugs. Another challenge posed by stockpiling of Tamiflu™ is that for the drug to be effective, it has to be given within 48 hours after exposure. Once the symptoms of infection appear the therapeutic efficacy of the drugs decreases dramatically. To better defend against influenza, whether seasonal and/or pandemic, there are compelling reasons to develop novel drugs or drug combinations that are safe, effective and less likely to give rise to drug-resistance.

Poly ICLC is a synthetic, double-stranded RNA (ds RNA) comprised of polyriboinosinic-polyribocytidylic (I:C) acid stabilized with poly-L-lysine and carboxymethylcellulose. Poly ICLC is a potent immunomodulating agent (Wong 2007). Liposome encapsulated Poly ICLC (LE Poly ICLC) was found to be a broadly effective prophylactic against a number of seasonal and avian influenza viruses in pre-exposure therapies (Wong 2007). LE Poly ICLC was also found to provide high level of protection in mice against highly pathogenic H5N1 avian influenza A virus. The window of protection provided by LE Poly ICLC was determined by pre-treating mice with 2 intranasal (IN) doses (1 mg/kg/dose) of LE Poly ICLC at day 1 to day 20 prior to infection with 10 $LD_{50}$ of influenza A/PR/8/34 virus. Although LE Poly ICLC when given to experimental animals in a pre-exposure prophylactic mode has been shown to provide complete protection against a number of influenza virus strains, including H5N1, H3N2 and H1N1 subtypes, its efficacy when administered in a post-exposure treatment mode after viral infection remains to be determined.

Ribonucleotide oligonucleotides (RNOs) are known to provide antiviral protection, including protection against influenza A viruses. Liposome encapsulated RNOs have been shown to be effective in the post-exposure treatment of mice infected with influenza A virus (Wong 2003). Other antisense oligonucleotides useful against influenza virus infections are know (Mizuta 1999; Zhang 2010).

There is a need in the art for new therapies against viral infections, in particular against influenza A virus.

SUMMARY OF THE INVENTION

Surprisingly, it has now been found that Poly ICLC or liposome-encapsulated Poly ICLC (LE Poly ICLC) in combination with antisense oligonucleotides (AS) act synergistically in post-exposure prophylaxis or therapy of influenza infections.

Thus, there is provided a method of treating an influenza virus infection in a subject comprising administering to the subject a synergistic combination of Poly ICLC or liposome-encapsulated Poly ICLC (LE Poly ICLC) and one or more antisense oligonucleotides (AS) after the subject has been exposed to the influenza virus.

There is further provided a use of a synergistic combination of Poly ICLC or liposome-encapsulated Poly ICLC (LE Poly ICLC) and one or more antisense oligonucleotides (AS) for treating an influenza virus infection in a subject after the subject has been exposed to the influenza virus.

There is further provided a pharmaceutical composition for post-exposure treatment of an influenza virus infection in a subject, the composition comprising a synergistic mixture of Poly ICLC or liposome-encapsulated Poly ICLC (LE Poly ICLC) and one or more antisense oligonucleotides (AS).

There is further provided a use of LE Poly ICLC for treating an influenza virus infection in a subject after the subject has been exposed to the influenza virus.

Poly ICLC is a large double-stranded RNA (ds RNA) that is greater than 200 nucleotides in length. It is a broad-spectrum drug what works against a wide range of influenza virus isolates. The mechanisms by which Poly ICLC elicits broad antiviral immune responses are mediated through recognition by and interaction with toll-like receptor-3 (TLR-3) on dendritic cells, monocytes and macrophages of the host's innate immunity (Wong 2009b). This recognition of ds RNA ligand by TLR-3 induces the production of interferon-$\alpha$, interferon-$\beta$ and interferon-$\gamma$ in vivo. This signaling pathway also plays a significant role for stimulation of both innate and adaptive immune responses, including the activation of natural killer cells.

Antisense oligonucleotides (AS) are short single-stranded highly virus-specific RNA/DNA oligomers. AS are preferably 13-25 nucleotides long, for example, about 15 nucleotides long. Antisense oligonucleolides mediate inhibiting of influenza A virus replication by a gene silencing approach. Haemagglutinin (HA) plays an important and essential role in the pathogenesis of influenza viral infection. Antisense oligonucleotides are capable of binding to the haemagglutinin (HA) gene, thereby inhibiting HA gene transcription, and/or are capable of binding to the transcribed HA mRNA, thereby inhibiting HA protein synthesis, and/or are capable of binding to the HA protein of the influenza virus particle itself, thereby inhibiting the action of HA protein, and effectively inhibiting viral replication and proliferation.

A variety of suitable antisense oligonucleotides are known in the art. For example, U.S. Pat. No. 6,544,958 discloses several suitable ribonucleotide oligonucleotides (RNOs). Antisense oligonucleotides may be unencapsulated or may be encapsulated in liposomes. Antisense oligonucleotides may comprise one or more modified bases, for example 2'-O-methyl RNA modified bases. Antisense oligonucleotides may comprise one or more non-nucleotide-based spacers, for example C1, C2, C3, C4 or C5 spacers. Preferred antisense oligonucleotides comprise SEQ ID NO: 1, SEQ ID NO: 2, SEQ ID NO: 3, chemically modified variants thereof (e.g. SEQ ID NO: 4) or mixtures thereof.

In addition to synergy, the present combination treatment offers a distinct advantage over conventional anti-influenza treatment with antiviral drugs in that the present combination treatment is more robust and less likely to give rise to drug resistance. Poly ICLC, including LE Poly ICLC, and antisense oligonucleotides work independently with distinct mechanisms of action as discussed above. It is therefore unlikely that influenza A viruses can simultaneously mutate to evade both of these mechanisms, especially since TLR-3 on the host's immune defense cell are not knows to mutate and change. Thus, due to its broad spectrum effect, Poly ICLC and LE Poly ICLC are well suited to provide an effective and robust antiviral agent that complements antisense oligonucleotides to combat seasonal, zoonotic and pandemic influenza viruses. Since Poly ICLC and LE Poly ICLC do not exert antiviral activity by specifically targeting influenza virus structure or protein, it is less likely to give rise to drug-resistance and may therefore offer protection against various influenza viruses, regardless of genetic mutations, reassortments, recombinations, zoonotic origin or drug-resistance.

Poly ICLC or LE Poly ICLC is typically used in an amount effective to treat the influenza virus infection. In combination with the one or more antisense oligonucleotides, the amount of Poly ICLC or LE Poly ICLC used is sufficient to act synergistically with the one or more antisense oligonucleotides. A suitable dosage of Poly ICLC or LE Poly ICLC may be within a range of from about 0.1 mg/kg body weight to about 5 mg/kg body weight, or about 0.5 mg/kg body weight to about 2 mg/kg body weight, for example about 1 mg/kg body weight. Antisense oligonucleotides are typically used in an amount effective to treat the influenza virus infection and to act synergistically with the Poly ICLC or LE Poly ICLC. A suitable dosage of AS may be within a range of from about 1 mg/kg body weight to about 50 mg/kg body weight, or about 5 mg/kg body weight to about 35 mg/kg body weight, for example about 20 mg/kg body weight.

Dosing regimes for a particular subject may be determined by a treating physician. Ideally, a first dose is administered to the subject as soon as possible after the subject has been exposed to the virus. However, it is a great advantage of the present combination therapy that treatment can be initiated well after initial exposure, for example 24 hours post-infection or even 48 hours post-infection, with the subject still having excellent survival prospects. Subjects may be dosed any suitable number of times per day, preferably 1-3 times per day, for example 1 time per day. Subjects may be further dosed in subsequent days. Preferably, subjects are dosed every day after the first dose for up to about 3 days.

The Poly ICLC or LE Poly ICLC and antisense oligonucleotides may be administered to a subject simultaneously or serially within a short period of time of each other. Preferably, Poly ICLC or LE Poly ICLC and the antisense oligonucleotides are part of the same pharmaceutical composition, but they can be administered separately provided they are administered within a time sufficient that the synergistic action is not lost. Typically, the time for clearing one of the compounds from the body is an extreme upper bound on the time to administer the other. However, administration of the other within 6 hours, more preferably 2 hours, even more preferably 1 hour, yet more preferably 30 minutes, of the first is preferred.

Any suitable administration method known in the art may be used. Some administration methods include intranasal, intravenous, intraarterial, subcutaneous or enteric. Intranasal administration is preferred. Preferred dosage forms for intranasal administration include aerosols, nasal sprays and nasal instillations. Active ingredients may be administered as part of a pharmaceutical composition "as is" or together with one or more pharmaceutically acceptable carriers, diluents or excipients. Active ingredients may form part of a kit or commercial package together with instructions for use in treating influenza virus infections.

The present post-exposure therapy is effective for treating seasonal and/or pandemic influenza infections. The therapy is useful against highly pathogenic avian influenza viruses. The therapy is particularly useful against known and emerging influenza A infections. Some examples of known influenza A infections are H1N1, H3N2, H5N1 and H5N2 infections. It is especially effective against H5N1 (e.g. HPA1) virus infections, which are often difficult to treat. The combination of LE Poly ICLC and antisense oligonucleotides is particularly effective.

Subjects that may be treated include animals, for example, mammals, birds (chickens, turkeys, pea fowl, etc.) and reptiles. Mammalian subjects include, for example, humans, horses, cows, sheep, goats, pigs, dogs, cats, rabbits, mice, hamsters, guinea pigs, monkeys, chimpanzees and rats.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Materials and Methods:

Female BALB/c mice (8-10 weeks old) were obtained from Vital River Laboratories (Beijing, China), and the original breeding pairs were purchased from Charles River. Mice were raised in IVC (independent ventilated cages) and received pathogen-free food and water.

Antisense oligonucleotides (AS) were prepared by Oligos Etc Inc. (Wilsonville, Oreg., USA). For all experiments, all AS were diluted in 0.9% sodium chloride made from RNAse-free water (Sigma, St. Louis, Mo.). The sequence of the AS used was as follows:

```
                                          (SEQ ID NO: 4)
     5'-mUmCmGmUmUmUmUmCmGmUmCmCmCmUX-3'
``` where m represents a 2'-O-methyl RNA modified base, and X is a C4 spacer (based on butanol).

Phospholipids and cholesterol used for the preparation of liposome-encapsulated Poly ICLC were purchased from Avanti Polar Lipids (Alabaster, Ala.). Large multilamellar vesicles (MLVs) were prepared using phosphatidylcholine, cholesterol and phosphatidyl glycerol in a molar ratio of 7:2:1, and were prepared using freeze drying procedures previously described (Wong 2007).

Example 1

Post-Exposure Treatment of Mice Exposed to Influenza A Virus

To evaluate the efficacy of LE Poly ICLC and antisense oligonucleotide combination treatment against highly pathogenic avian influenza (H5N1) viral infection, groups of 8 to 10 BALB/c mice were randomly assigned as either negative control animal group (saline only), LE Poly ICLC only animal group or LE Poly ICLC and AS animal group. The groups were then challenged by intranasally infecting them with 5 $LD_{50}$ of influenza/H5N1/Henan/chicken (a representative HPA1) virus.

At 30 minutes post virus challenge, a negative control group was treated intranasally with phosphate buffered saline, an LE Poly ICLC alone group was treated intranasally with LE Poly ICLC (1 mg/kg body weight/dose) and an LE Poly ICLC and AS group was treated with LE Poly ICLC (1 mg/kg body weight/dose) and AS (20 mg/kg body weight/dose), followed by intranasal administration once per day for three days at the same dose. At 24 hours post virus challenge, another negative control group, another LE Poly ICLC alone group and another LE Poly ICLC and AS group were dosed using the same dosing regime as above. The volume of the inoculum in all cases was 50 µl. The animals were then monitored daily for symptoms of infection, body weight and survival. At day 14 post infection, the number of mice which survived the virus infection in each group was recorded. Survival patterns of the mice were graphed using the Log-rank test (GraphPad Prism version 4.01, San Diego, Calif.). Differences were considered significant at $p<0.05$.

Figure 1A:
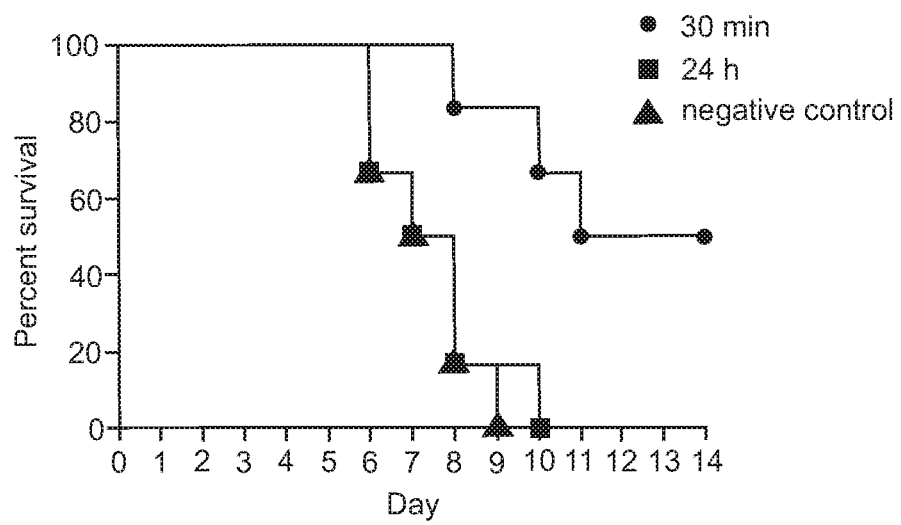
In FIG. 1A, survival of six mice in each group was observed for 14 days post-infection and data are expressed as percentages of total survival. For FIG. 1B, three mice in each group were euthanized on day 4 post-infection and viral titers in lung were determined by plaque assay and Real-time PCR (*, $p<0.001$).
Figure 1B:
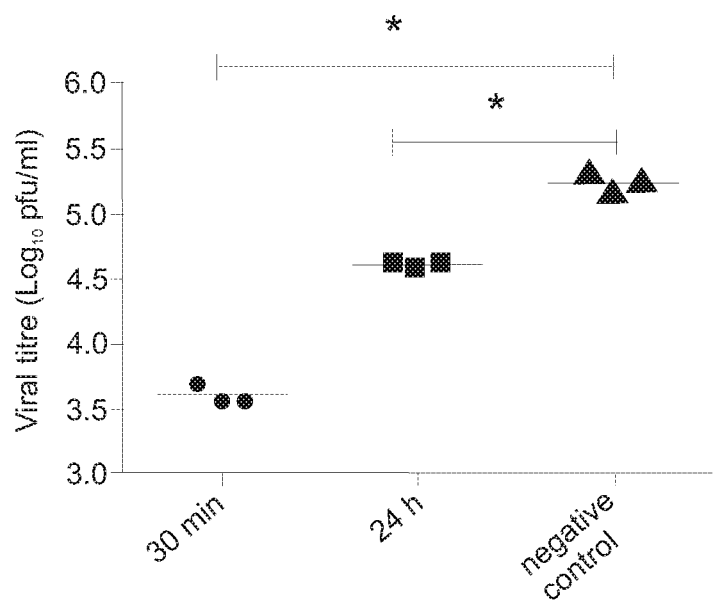
FIG. 1 depicts graphs showing therapeutic effect of post-exposure treatment with LE Poly ICLC alone (1 mg/kg body weight) on mice infected intranasally with 5 $LD_{50}$ H5N1 virus. Post-exposure treatments were done at 30 min post-infection or 24 hours post-infection, followed by treatment at same dose once per day for three days.

Although previously published results have demonstrated that LE Poly ICLC has a prophylactic effect on controlling H5N1 viral replication in vivo when administered to subjects prior to viral exposure (Wong 2007), there has been no previous report on its therapeutic efficacy in post-exposure treatment. In the present example, the LE Poly ICLC alone group provides results for the effect of LE Poly ICLC in post-exposure treatment. The results (FIG. 1A) show that 50% of the mice that were treated with LE Poly ICLC 30 min post infection survived to 14 days post infection, while the mice treated 24-hour post infection all died by 10 days post infection. All of the mice in the negative control group died by 9 days post infection. This reflects the importance of treatment timing when using LE Poly ICLC alone as a post-exposure therapeutic agent. Pulmonary viral titer, as measured in by plaques in MDCK cells in lung tissues of the animals, showed a similar trend to survival rate (FIG. 1B).

Figure 2:
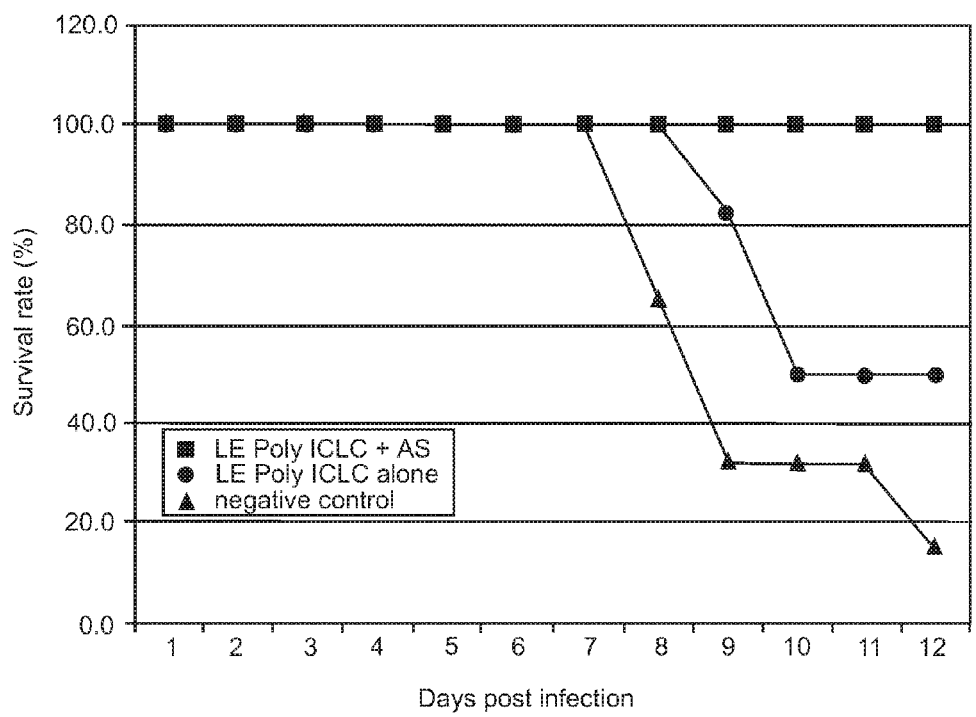
FIG. 2 depicts a graph showing therapeutic effect of post-exposure combination treatment of LE Poly ICLC (1 mg/kg body weight) and antisense oligonucleotide (SEQ ID NO: 4, 20 mg/kg body weight) on mice infected intranasally with 5 $LD_{50}$ H5N1 virus. Post-exposure treatments were done at 24 hours post-infection, followed by treatment at same dose once per day for three days. Survival of six mice in each group was observed for 14 days post-infection and data are expressed as percentages of total survival.
Figure 3:
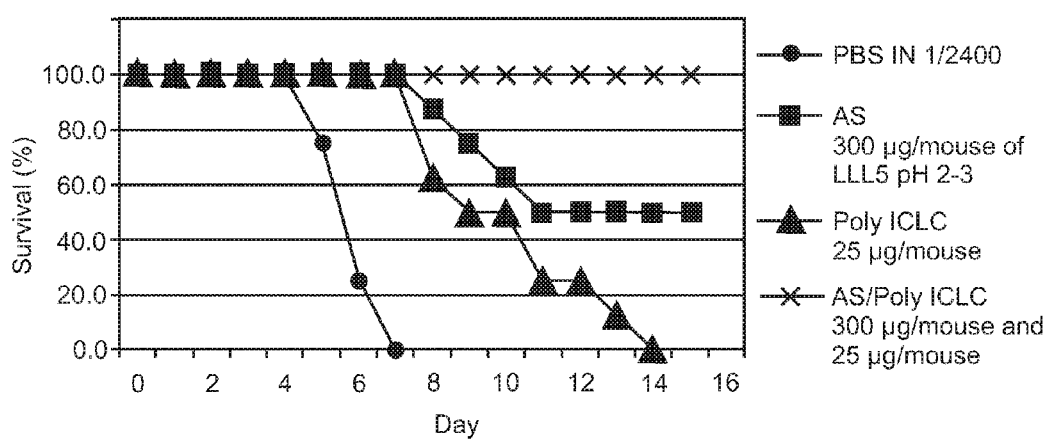
FIG. 3 depicts a graph showing synergistic effect of Poly ICLC and antisense oligonucleotide (SEQ ID NO: 4) for the post exposure treatment of influenza A/PR/8/34 virus in mice.
Figure 4:
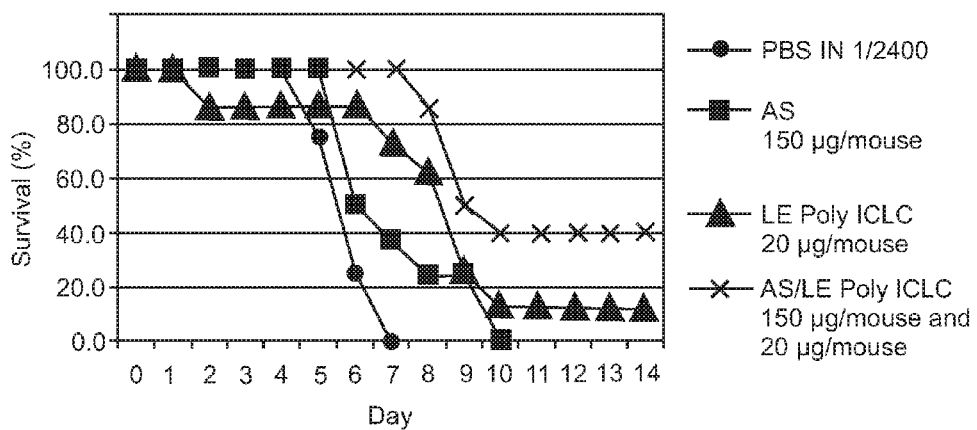
FIG. 4 depicts a graph showing synergistic effect of low dose of LE Poly ICLC and antisense oligonucleotide (SEQ ID NO: 4) for the post exposure treatment of influenza A/PR/8/34 virus in mice.
Figure 5:
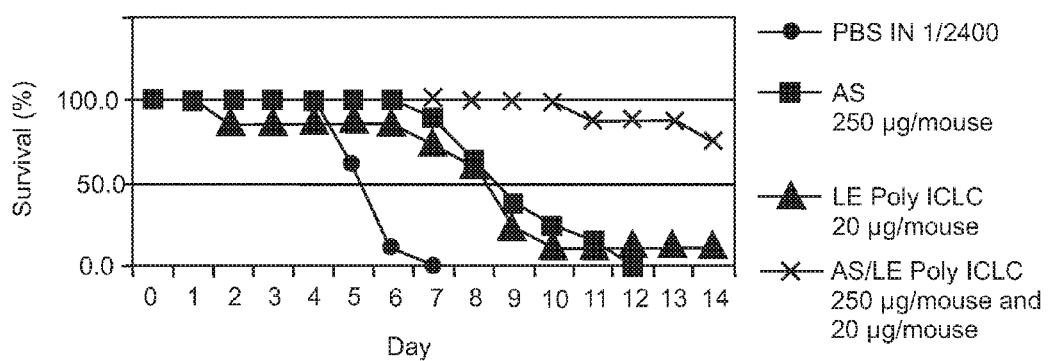
FIG. 5 depicts a graph showing synergistic effect of high dose of LE Poly ICLC and antisense oligonucleotide (SEQ ID NO: 4) for the post exposure treatment of influenza A/PR/8/34 virus in mice.

Therapeutic efficacy of a combination treatment 24 hours post-infection using LE Poly ICLC and antisense oligonucleotides is shown in FIG. 2 in comparison to the negative control group (saline only) and the LE Poly ICLC alone group. The results showed that treatment with LE Poly ICLC alone at 24 hours post-infection was only partially effective resulting in 50% survival rate. However, when combined with antisense oligonucleotide (SEQ ID NO: 4), all of the H5N1 infected animals survived the virus challenge (100% survival, $p<0.001$ vs. negative control). That all treated animals given a combination of LE Poly ICLC and antisense oligonucleotide were completely protected against an unnaturally high virus challenge evidences the synergism of this combination in treating H5N1 virus infection.

Example 2

Synergistic Effect of Poly ICLC or LE Poly ICLC Together with Antisense Oligonucleotides Against Influenza A/PR/8/34 (H1N1) Virus Infection Therapeutic efficacies of combination treatment using free Poly ICLC or LE Poly ICLC and antisense oligonucleotides (AS) were further evaluated to confirm that free Poly ICLC or LE Poly ICLC act synergistically with antisense oligonucleotides to treat influenza A/PR/8/34 virus infection in mice.

Mice were challenged with 5 $LD_{50}$ influenza A/PR/8/34 (H1N1) virus, and then intranasally given free Poly ICLC (1.2 mg/kg), LE Poly ICLC (1.2 mg/kg), antisense oligonucleotide (SEQ ID NO: 4, 15 mg/kg), a combination of free Poly ICLC and antisense oligonucleotide, or a combination of LE Poly ICLC and antisense oligonucleotide at 1 and 4 hours post infection.

Post exposure treatment of influenza A infection using free Poly ICLC alone (1.2 mg/kg) was not effective and did not result in any increased survival while antisense oligonucleotide provided a 50% survival rate (FIG. 3). However, when infected mice were treated with a combination of free Poly ICLC and SEQ ID NO: 4, all treated mice survived the virus infection while all PBS control treated mice died from infection (FIG. 3) ($p<0.01$). The 100% survival rate with combination treatment was higher than the combined survival rates from single treatments with Poly ICLC and SEQ ID NO: 4, indicating synergistic therapeutic effect obtained with combination therapy with Poly ICLC and SEQ ID NO: 4.

Similarly, antisense treatment at a lower dose of SEQ ID NO: 4 (150 μg/mouse) was not effective (0% survival), and neither was LE Poly ICLC (20 μg/mouse, 10% survival), but combined therapy using these doses of LE Poly ICLC and SEQ ID NO: 4 provided a synergistic increased survival rate of 40% (FIG. 4).

Similar results were observed at the same dose of LE Poly ICLC (20 μg/mouse) and higher doses of SEQ ID NO: 4 (250 μg/mouse) given singly or in combination therapy (FIG. 5). Single treatment with SEQ ID NO: 4 (0% survival) and LE Poly ICLC (10%) was not very effective, while combination therapy with LE Poly ICLC and SEQ ID NO: 4 resulted in significantly high synergistic therapeutic efficacy of more than 70% (FIG. 5).

Free Listing of Sequences:

| SEQ ID | Sequence |
|---|---|
| SEQ ID NO: 1 | 5' UCC CCU GCU UUU GCU 3' (15 nucleotides, from U.S. Pat. No. 6,544,958) |
| SEQ ID NO: 2 | 5' AGC AAA AGC AGG GGA 3' (15 nucleotides, from U.S. Pat. No. 6,544,958) |
| SEQ ID NO: 3 | 5' UCG UUU UCG UCC CCU 3' (15 nucleotides, from U.S. Pat. No. 6,544,958) |
| SEQ ID NO: 4 | 5' mUmCmG mUmUmU mUmCmG mUmCmC mCmCmU X 3' (15 nucleotides, 2'-O-methyl modified, X is a C4 spacer) |

REFERENCES

The contents of the entirety of each of which are incorporated by this reference.

Andre F, Zitvogel L, Sabourin J-C. (2008) United States Patent Publication 2008-0317811 published Dec. 25, 2008.

Andre F, Zitvogel L, Sabourin J-C. (2010) Treatment of Cancer Using TLR3 Agonists. United States Patent Publication 2010-0266680 published Oct. 21, 2010.

Bright R A, Medina M J, Xu X, et al. (2005) Incidence of adamantine resistance among influenza A (H3N2) viruses isolated worldwide from 1994 to 2005: a cause for concern. *Lancet.* 366(9492), 1175-1181.

de Jong M D, Tran T T, Truong H K, et al. (2005) Oseltamivir resistance during treatment of influenza A (H5N1) infection. *N Engl. J. Med.* 353(25), 2667-2672.

Dharan N J, Gubareva L V, Meyer J J, et al. (2009) Infections with oseltamivir-resistant influenza A (H1N1) virus in the United States. *JAMA.* 301(10), 1034-1041.

Dow S. (2008) Liposome-nucleic acid immunotherapeutics. *Expert Opinion on Drug Delivery.* 5(1), 11-24.

Haixiang L. (2007) Polyinosinic Acid-Polycytidilic Acid-Based Adjuvant. United States Patent Publication 2007-0160632 published Jul. 12, 2007.

Jeffs R, Gotzkowsky S K, Dwek R A, Zitzmann N. (2008) Combination Therapy for Treatment of Viral Infections. United States Patent Publication 2008-0131398 published Jun. 5, 2008.

Johansen L M, Owens C M, Mawhinney C, Chappell T W, Brown A T, Frank M G, Altmeyer R, Chen Y. (2008) Compositions and Methods for Treatment of Viral Diseases. United States Patent Publication 2008-0161324 published Jul. 3, 2008.

Johansen L M, Owens C M. (2010a) Compositions and Methods for Treatment of Viral Diseases. United States Patent Publication 2010-0092479 published Apr. 15, 2010.

Johansen L M, Owens C M, Mawhinney C, Chappell T W, Brown A T, Frank M G, Foley M A, Altmeyer R, Chen Y. (2010b) Compositions and Methods for Treatment of Viral Diseases. United States Patent Publication 2010-0009970 published Jan. 14, 2010.

Kumar A, Zarychanski R, Pinto R, et al. (2009) Critically ill patients with 2009 influenza A (H1N1) infection in Canada. JAMA. 302(17), 1872-1879.

Mizuta T, Fujiwara M, Hatta T, Abe T, Miyano-Kurosak N, Shigeta S, Yokota T, Takaku H. (1999) Antisense oligonucleotides directed against the viral RNA polymerase gene enhance survival of mice infected with influenza A. *Nature Biotechnology.* 17, 583-587.

Nguyen J, Went G T, Spence P, Fultz T J, Chernoff D, Burkoth T L, Chapman R, Urdea M S. (2009) Compositions and Kits for Treating Influenza. United States Patent Publication 2009-0247481 published Oct. 1, 2009.

Salazar A. (2005) Method for Preparation of Poly-ICLC and Uses Thereof. International Patent Publication WO 2005-102278 published Nov. 3, 2005.

Salazar A M. (2006) Clinical Method for the Immunomodulatory and Vaccine Adjuvant of Poly ICLC and Other dsRNAs. United States Patent Publication 2006-223742 published Oct. 5, 2006.

Salazar A. (2009) Method for Therapeutic, Clinical and Veterinary Use of Poly ICLC. United States Patent Publication 2009-087454 published Apr. 2, 2009.

Saravolac E G, Wong J P. (2007) Recent Patents on Development of Nucleic Acid-based Antiviral Drugs against Seasonal and Pandemic Influenza Virus Infections. *Recent Patents on Anti-Infective Drug Discovery*. 2, 140-147.

Sharma G, Altmeyer R, Pendharker V, Chen Y, Foley M. (2010) Compositions and Methods for Treating Viral Infections. United States Patent Publication 2010-0081713 published Apr. 1, 2010.

Wong J P, Saravolac E G, Sabuda D, Levy H B, Kende, M. (1995) Prophylactic and therapeutic efficacies of poly(I-CLC) against respiratory influenza A virus infection in mice. *Antimicrob. Agents Chemother.* 39, 2574-2576.

Wong J P H. (2001) Liposome-Encapsulated Poly ICLC. United States Patent Publication 2001-0007667 published Jul. 12, 2001.

Wong J P H. (2002) Liposome-Encapsulated Poly ICLC. U.S. Pat. No. 6,468,558 issued Oct. 22, 2002.

Wong J P H, Nagata L P. (2003) Therapy of Respiratory Influenza Virus Infection Using Free and Liposome-Encapsulated Ribonucleotides. U.S. Pat. No. 6,544,958 issued Apr. 8, 2003.

Wong J P, Christopher M E, Salazar A M, Dale R M K, Sund L-Q, Wang M. (2007) Nucleic acid-based antiviral drugs against seasonal and avian influenza viruses. *Vaccine*. 25, 3175-3178.

Wong J P, Christopher M E, Viswanathana S, Karpoff N, Daia X, Dasa D, Sun L Q, Wang M, Salazar A M. (2009a) Activation of toll-like receptor signaling pathway for protection against influenza virus infection. *Vaccine*. 27, 3481-3483.

Wong J P, Christopher M E, Viswanathan S, Dai X, Salazar A M, Sun L-Q, Wang M. (2009b) Antiviral Role of Toll-Like Receptor-3 Agonists Against Seasonal and Avian Influenza Viruses. *Current Pharmaceutical Design*. 15(11), 1269-1274.

Wong J. (2009c) Liposome Encapsulated Poly ICLC Method to Prophylatically Treat an Avian Influenza Viral Infection. United States Patent Publication 2009-0214638 published Aug. 27, 2009.

Zhang T, Zhao P, Zhang W, Liang M, Gao Y, Yang S, Wang T, Qina C, Wang C, Xia X. (2010) Antisense oligonucleotide inhibits avian influenza virus H5N1 replication by single chain antibody delivery system. *Vaccine*. doi:10.1016, 7 pages.

Zhao G, Lu J, Glass J I, Martinez A, Yan Y. (2003) Oligonucleotide Therapeutics for Treating Hepatitis C Virus Infections. International Patent Publication WO 2003-016572 published Feb. 27, 2003.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A method of treating an influenza virus infection in a subject consisting essentially of administering to the subject, after the subject has been exposed to the influenza virus, a synergistic combination of
   Poly ICLC or liposome-encapsulated Poly ICLC (LE Poly ICLC), and
   an antisense oligonucleotide comprising the nucleotide sequence as set forth in SEQ ID NO: 4.

2. The method of claim 1, wherein the synergistic combination comprises the LE Poly ICLC and the antisense oligonucleotide comprising the nucleotide sequence as set forth in SEQ ID NO: 4.

3. The method of claim 2, wherein the influenza virus is an influenza A virus.

4. The method of claim 2, wherein the influenza virus is H1N1, H3N2, H5N1 or H5N2 virus.

5. The method of claim 2, wherein the influenza virus is H5N1 virus.

6. The method of claim 2, wherein the antisense oligonucleotide is administered in liposome-encapsulated form.

7. The method of claim 2, wherein the LE Poly ICLC is administered in an amount in a range of from 0.1 to 5 mg/kg body weight of the subject.

8. The method of claim 2, wherein the antisense oligonucleotide is administered in an amount in a range of from 1 to 50 mg/kg body weight of the subject.

9. The method of claim 2, wherein the LE Poly ICLC and the antisense oligonucleotide are administered to the subject within 2 hours of each other.

10. The method of claim 2, wherein the LE Poly ICLC and the antisense oligonucleotide are administered to the subject simultaneously.

11. The method of claim 2, wherein the LE Poly ICLC and the antisense oligonucleotide are administered intranasally.

12. The method of claim 11, wherein intranasal the administration is accomplished with an aerosol.

13. The method of claim 2, wherein the subject is human.

* * * * *

SEQUENCE LISTING

```
<160> NUMBER OF SEQ ID NOS: 4

<210> SEQ ID NO 1
<211> LENGTH: 15
<212> TYPE: RNA
<213> ORGANISM: Artificial Sequence
<220> FEATURE:
<223> OTHER INFORMATION: Antisense oligonucleotide

<400> SEQUENCE: 1
uccccugcuu uugcu                                                    15

<210> SEQ ID NO 2
<211> LENGTH: 15
<212> TYPE: RNA
<213> ORGANISM: Artificial Sequence
<220> FEATURE:
<223> OTHER INFORMATION: Antisense oligonucleotide

<400> SEQUENCE: 2
agcaaaagca gggga                                                    15

<210> SEQ ID NO 3
<211> LENGTH: 15
<212> TYPE: RNA
<213> ORGANISM: Artificial Sequence
<220> FEATURE:
<223> OTHER INFORMATION: Antisense oligonucleotide

<400> SEQUENCE: 3
ucguuuucgu ccccu                                                    15

<210> SEQ ID NO 4
<211> LENGTH: 15
<212> TYPE: RNA
<213> ORGANISM: Artificial Sequence
<220> FEATURE:
```

```
<223> OTHER INFORMATION: Antisense oligonucleotide
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(7)
<223> OTHER INFORMATION: um
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(14)
<223> OTHER INFORMATION: cm
<220> FEATURE:
<221> NAME/KEY: modified_base
<222> LOCATION: (15)..(15)
<223> OTHER INFORMATION: um

<400> SEQUENCE: 4 ucguuucgu ccccu                                            15
```